(12) United States Patent
Miyagawa

(10) Patent No.: US 7,260,978 B2
(45) Date of Patent: Aug. 28, 2007

(54) GAS CHROMATOGRAPHY/MASS SPECTROMETRY SYSTEM

(75) Inventor: Haruhiko Miyagawa, Kyoto (JP)

(73) Assignee: Shimadzu Corporation, Kyoto-shi (JP)

( * ) Notice: Subject to any disclaimer, the term of this patent is extended or adjusted under 35 U.S.C. 154(b) by 77 days.

(21) Appl. No.: 11/269,606

(22) Filed: Nov. 9, 2005

(65) Prior Publication Data

US 2006/0123883 A1  Jun. 15, 2006

(30) Foreign Application Priority Data

Dec. 9, 2004  (JP) .............................. 2004-357029

(51) Int. Cl.
*G01N 30/02* (2006.01)
*G01N 30/06* (2006.01)
*B01D 53/14* (2006.01)

(52) U.S. Cl. .................. 73/23.37; 73/23.41; 73/23.42; 95/82; 95/85; 95/86; 95/87; 96/101; 96/104; 96/105; 96/106

(58) Field of Classification Search ............... 73/23.37, 73/23.41, 23.42; 95/82, 85, 86, 87, 88; 96/101, 96/104, 105, 106

See application file for complete search history.

(56) References Cited

U.S. PATENT DOCUMENTS

| 6,494,939 | B1 * | 12/2002 | Tipler ........................... 96/105 |
| 6,749,749 | B2 * | 6/2004 | Xie et al. ................. 210/198.2 |
| 2005/0211098 | A1 * | 9/2005 | Shimomura .................. 96/101 |

* cited by examiner

*Primary Examiner*—Daniel S. Larkin
(74) *Attorney, Agent, or Firm*—Manaba Kanesaka

(57) ABSTRACT

A gas chromatography/mass spectrometry system includes two sample introduction parts, a gas chromatography part having two columns, a column oven for housing the two columns in a parallel configuration, an interface part through which an outlet end of each of the two columns is inserted, and a mass spectrometry part. The mass spectrometry part has an ionization chamber to which the outlet ends of the columns inserted through the interface part are connected, a mass separation part, an ion detector, and a vacuum chamber for housing the ionization chamber, the mass separation part, and the detector. Because the outlet ends of the parallel columns are both connected to the ionization chamber, the carrier gas flow and line velocity are the same as though there is one column, thereby avoiding line stagnation. Since analyses can be performed selectively with a single system, results having high reliability and precision can be obtained.

6 Claims, 2 Drawing Sheets

GAS CHROMATOGRAPHY/MASS SPECTROMETRY SYSTEM

BACKGROUND OF THE INVENTION AND RELATED ART STATEMENT

The present invention relates to a gas chromatography/mass spectrometry system that includes a gas chromatograph and a mass spectrometer.

Recently, gas chromatography/mass spectrometry systems ("GC/MS") combining gas chromatographs and mass spectrometers have been widely used for identification analysis and quantification analysis of various kinds of samples. See, for example, the system disclosed in Japanese Unexamined Patent Publication No. H10-283982.

In a GC/MS, when introducing sample gases into the column of the GC part, various kinds of sample introduction devices are used in accordance with the types and properties of the samples. For example, when analyzing agricultural chemicals, and in environmental analyses, a liquid sample introduction device is used which gasifies the liquefied sample inside a high-temperature sample gasification chamber and sends it into the column.

Also, when analyzing volatile organic compounds ("VOC"), such as trichloroethylene, and the like, a headspace sample introduction device is used. The headspace sample introduction device collects a specified quantity of sample gas volatized from a liquid sample stored in a container, and sends the volatized gas to the column.

Also, because it is necessary to also change the separation properties of the columns used for component analysis between agricultural chemicals and volatile organic compounds, the columns that are used are themselves different when using a liquid sample introduction device and when using a headspace sample introduction device.

Therefore, in an organization that must analyze both agricultural chemicals and volatile organic compounds, such as environmental analysis research institutions, it is desirable to have a GC/MS having a liquid sample introduction device and an associated column suitable for agricultural chemical analysis, and a GC/MS having a headspace sample introduction device and an associated column suitable for volatile organic compound analysis. Then, the systems can be prepared respectively in advance, and the analysis can be performed by selecting either device in accordance with the sample to be analyzed.

However, because preparing two GC/MS's is expensive, a conventional approach has been to perform agricultural chemical analysis and volatile organic compound analysis by suitably switching with one GC/MS. In the past, although there have been gas chromatography devices configured such that a liquid sample introduction device and a headspace sample introduction device can be arranged in parallel, it was still necessary to attach a column suitable for the respective analysis. That is, depending on whether a liquid sample introduction device or a headspace sample introduction device is used, it was necessary to attach a column between the sample gas outlet end of the liquid sample introduction device or the headspace sample introduction device, and a GC/MS interface.

Therefore, when switching, for example, from agricultural chemical analysis to volatile organic compound analysis, it has been necessary to replace the column inside the column oven. This is done by temporarily stopping the device and returning the vacuum chamber of the mass spectrometer to approximately atmospheric pressure. Such operations take effort and time, and the analytical efficiency is degraded. Also, as a result of repeated stopping and starting of the device, instabilities easily arise. For example, the inside of the vacuum chamber of the mass spectrometer may be contaminated by components in the air, and the reliability of analysis may be lowered.

Also, when analyzing volatile organic compounds in water, a purge/trap sample introduction device also may be used in place of the headspace sample introduction device. A purge/trap sample introduction device forcefully drives out volatile organic compounds and mold odors, and the like, in the water by blowing purge gas into a custom test tube in which sample water is collected, and temporarily retains the driven-out components in an adsorbent material. After that, the sample components are separated from the adsorbent material by heating them off, and they are then introduced into the column. Also, when it is desirable to selectively use such a sample introduction device with a liquid sample introduction device or headspace sample introduction device, the same problems as those described above also arise.

The present invention addresses the aforementioned problems associated with the prior art devices.

One object of the present invention is to provide a gas chromatography/mass spectrometry system that can perform analysis of samples of different kinds and different properties, such as analysis of agricultural chemicals, and the like, and analysis of volatile organic compounds, and the like, with one system using columns suitable for each.

Another object of the present invention is to provide a gas chromatography/mass spectrometry system that can perform the above-described two kinds of analysis continuously without requiring the annoying work of changing columns, and without temporarily stopping the device.

Further objects and advantages of the invention will be apparent from the following description of the invention and the associated drawings.

SUMMARY OF THE INVENTION

The gas chromatography/mass spectrometry system according to the present invention solves the aforementioned problems associated with prior art devices.

The system includes a) two sample introduction parts, a first and a second part, that are of mutually opposite types or are of the same type; b) a gas chromatography part, which includes a first column for separating a sample component in the course of causing a sample gas introduced from the first sample introduction part to flow through, a second column for separating a sample component in the course of causing a sample gas introduced from the second sample introduction part to flow through, and a column oven which is capable of accommodating the two columns in parallel; c) an interface part including a temperature maintenance block, through which the outlet side ends of the first and second columns are both inserted; and d) a mass spectrometry part.

The mass spectrometry part includes an ionization chamber to which the outlet ends of the first and second columns inserted through the interface part are connected, a mass separation part for mass-separating ions produced inside the ionization chamber, and a detector for detecting the mass-separated ions, all of which are located inside a vacuum chamber.

The first and second sample introduction parts can include such suitable ones as various kinds of liquid sample introduction devices with a split system, a splitless system, and the like, and headspace sample introduction devices, purge/trap sample introduction devices, and the like. The first and second sample introduction parts can be selected in accordance with the types, forms, and properties of the samples to be analyzed. Also, for the first and second columns, columns of a type corresponding to the target samples introduced by the first and second sample introduction parts should be used.

In one embodiment of the gas chromatography/mass spectrometry system according to the present invention, the first sample introduction part is a headspace sample introduction part, which collects and delivers sample gas from a space above the liquid surface of a liquid sample stored inside a container. The second sample introduction part is a liquid sample introduction part, which includes a sample gasification chamber for gasifying an injected liquid sample inside it.

With the aforementioned configuration, for example, a column having high polarity, which is suitable for the separation of components of volatile organic compounds can be used as the first column, and a column having no polarity or low polarity, which is suitable for the separation of agricultural chemicals, and the like, can be used as the second column. Because the outlet ends of the first and second columns are directly connected to the ionization chamber under a vacuum atmosphere, the column flow amount must be relatively small, and thin-diameter capillary columns are used for the two columns.

In the above-described embodiment of the gas chromatography/mass spectrometry system, which might be used, for example, in the environmental analysis field, a headspace sample introduction part suitable for analysis of volatile organic compounds and a first column, and a liquid sample introduction part suitable for analysis of agricultural chemicals, and a second column, are arranged in parallel. The outlet ends of the two columns are both connected to the ionization chamber of the mass spectrometry part by way of the interface part.

Accordingly, either of the two above-described combinations is selected in accordance with the type of sample that is the subject of analysis, the sample gas is introduced into the first or second column from the selected sample introduction device, and the sample gas component separated by that column is analyzed by the mass spectrometry part.

At the same time, a flow of carrier gas is also routed through the column not being used, i.e., the one in which the sample gas has not been introduced. The carrier gas is used not only for column protection, but because the outlet ends of the two columns are directly connected to the ionization chamber (i.e., without being connected mid-course or without having a switching valve placed in between), and therefore the outlet ends of both columns are in a vacuum environment. Thus, for each of the two columns, the carrier gas flow amount and the line velocity can be calculated just as when there is a single column. In addition, the desired retention time of the sample component passing through the column can be set without considering the influence of the line velocity of the carrier gas in the other column.

By virtue of the gas chromatography/mass spectrometry system according to the present invention, the analysis of samples of different types and different properties, such as, for example, agricultural chemicals and volatile organic compounds, can be performed selectively with one system. Even when different analyses are to be performed, by controlling the combination of sample introduction parts and columns, the analyses can be performed virtually continuously, without having to temporarily stop the device. Therefore, the analyses can be performed efficiently while controlling the expense associated with introduction of the samples to the system. Furthermore, even when performing different analyses, because there is no need to repeatedly start and stop the device, analytical results having high reliability can be obtained by virtue of the ability to maintain stability of the mass spectrometer.

Furthermore, because in the gas chromatography/mass spectrometry system of the present invention the outlet ends of the two columns arranged in parallel are both connected to the ionization chamber, the carrier gas flow amount and the line velocity are the same as when there is one column. In addition, the retention time of each sample is the same as in the case of one column. Also, because there is no flow channel switching valve, or the like, on the outlet ends of the columns, there also is no concern that dead volume will arise due to such a valve. This too is advantageous for obtaining results having high precision.

DETAILED DESCRIPTION OF THE PREFERRED EMBODIMENTS

In the following description, a GC/MS system according to one embodiment of the present invention is described with reference to the accompanying drawings.

Figure 1:
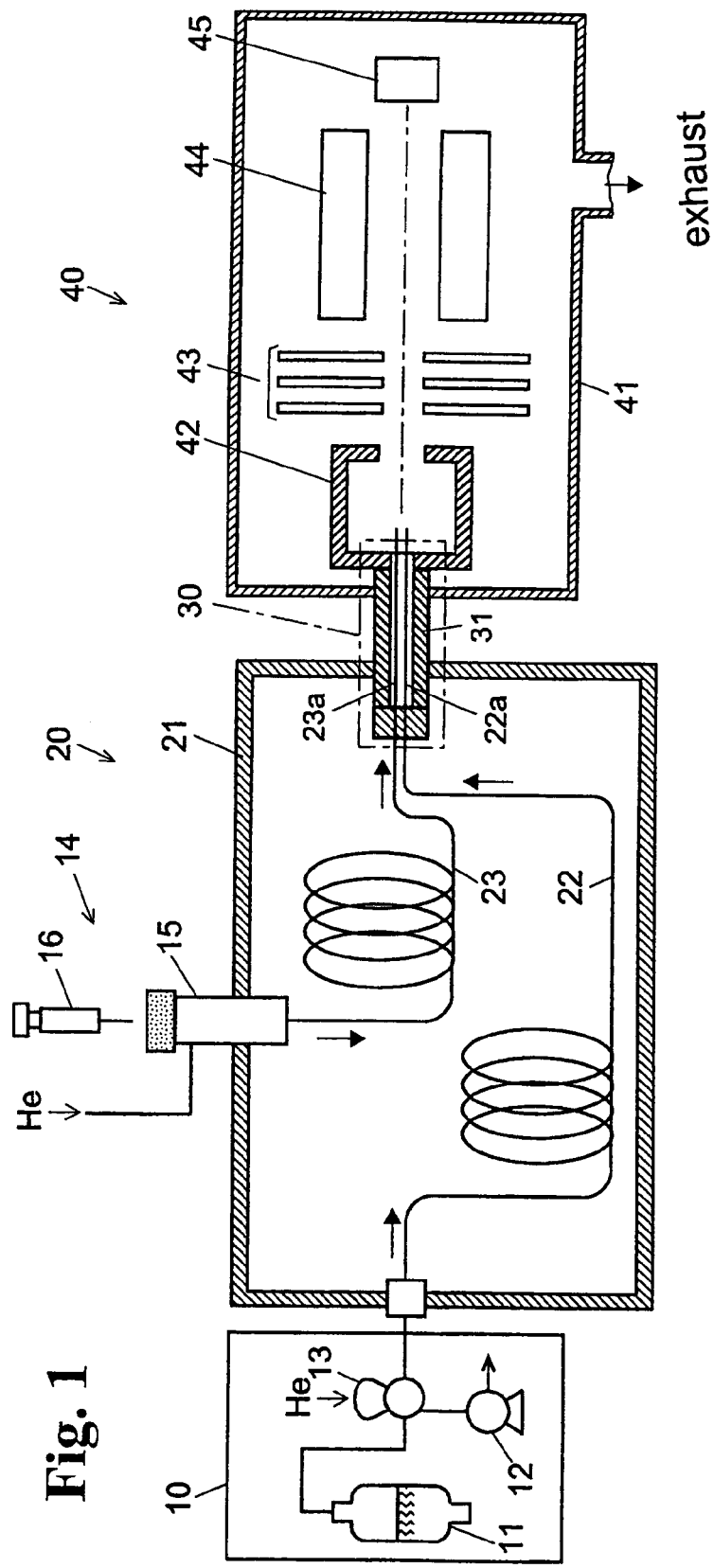
FIG. 1 is a schematic diagram of the structural components of a GC/MS system according to one embodiment of the present invention.

FIG. 1 is a schematic diagram of the components of a GC/MS system according to one embodiment of the present invention. In a GC (gas chromatography) part 20, two first and second capillary columns (below, simply described as "columns") 22, 23 are located inside a column oven 21. The inlet end of the first column 22 is connected to a headspace sample introduction device 10, and the inlet end of the second column 23 is connected to a splitless type sample gasification chamber 15 of a liquid sample introduction device 14.

The headspace sample introduction device 10 includes a container 11 for storing a liquid sample, a pump 12 for aspirating a sample gas, an aspiration retention part 13 for retaining a fixed quantity of sample gas aspirated from the headspace inside the container 11. At times other than when the above-described sample gas is being supplied to the first column 22, a carrier gas (e.g., helium) is supplied in a fixed flow amount to the first column 22.

Meanwhile, in the liquid sample introduction device 14, a fixed quantity of carrier gas is supplied to the second column 23 and passes through the sample gasification chamber 15, which is heated to a high temperature. When a liquid sample is injected into the sample gasification chamber 15 from an injector 16, the injected liquid sample is first gasified, and is then introduced into the second column 23 by being swept in the carrier gas flow.

The first and second columns 22, 23 are heated to a suitable temperature by the column oven 21, and each sample component is separated over time as the sample gas introduced into the columns 22, 23 pass through each column 22, 23.

The outlet side ends 22a, 23a of the first and second columns 22, 23 are extended by way of an interface part 30 to the interior of an ionization chamber 42 of a mass spectrometry (MS) part 40. In the MS part 40, the ionization chamber 42, as well as an ion lens 43, a quadrupole mass filter 44 as a mass analyzer, and a detector 45 are sequentially arranged according to the direction of travel of ions inside a vacuum chamber 41, which is evacuated.

A primary function of the interface part 30 located between the GC part 20 and the MS part 40 is to ensure that the flow of sample gas introduced into the ionization chamber does not stagnate. This is accomplished in part by maintaining the temperature of the outlet side ends 22a, 23a of the first and second columns 22, 23 at the same temperature as that inside the column oven 21. To maintain this temperature, a tubular heater unit 31, or the like, is provided.

The outlet side ends 22a, 23a of the first and second columns 22, 23 extend to the ionization chamber 42, and are inserted in parallel through the heater 31. The outlet ends of the columns 22, 23 are opened toward the inside of the ionization chamber 42.

The sample gas, which is, as described above, component-separated when passing through the first and second columns 22, 23, flows from the outlet ends into the ionization chamber 42. In the ionization chamber 42, the sample molecules are ionized by an ionization method, such as, for example, electron impact ionization, chemical ionization, and the like. The generated ions are led out of the ionization chamber 42, collected by the ion lens 43, and introduced to the quadrupole mass filter 44. Voltage overlapping direct current voltage and high-frequency voltage is applied to the quadrupole mass filter 44 by a power circuit (not illustrated).

Only ions having a mass number corresponding to the applied voltage pass through a space in the long axial direction of the quadrupole mass filter 44 and reach the detector 45. That is, the mass number of the ions that can pass through the quadrupole mass filter 44 changes as the voltage applied to the quadrupole mass filter 44 is changed. Therefore, a mass spectrum representing the relationship between the mass numbers and the ion strengths can be obtained by detecting the size of the current corresponding to the number of ions reaching the detector 45 at a particular time.

In the GC/MS system according to the above-described embodiment of the present invention, the combination of the headspace sample introduction device 10 and the first column 22 is used for analysis of volatile organic compounds. The combination of the liquid sample introduction device 14 and the second column 23 is used for analysis of agricultural chemicals. Therefore, the first column 22 is generally a capillary column having high polarity, which is suitable for analysis of volatile organic compounds, such as trichloroethylene.

The second column 23 is generally a capillary column having no polarity, which is suitable for analysis of chlorine agricultural chemicals, pyrethroids, organic phosphorus agricultural chemicals, nitrogen agricultural chemicals, and carbamate agricultural chemicals.

In the above-described configuration, when analyzing agricultural chemicals, the liquid sample prepared in the injector 16 is injected into the sample gasification chamber 15, and the sample gas is introduced to the second column 23 by being swept in the carrier gas flow. At this point, in the headspace sample introduction device 10, only a small quantity of carrier gas is flowed into the first column 22.

In the second column 23 (i.e., the column to which the sample gas was introduced), the sample components are separated, and the sample components successively flow into the ionization chamber 42. Mass analysis of each sample component is then performed by the MS part 40.

At this point, because no sample has been introduced into the first column 22, analysis of only the sample prepared in the liquid sample introduction device 14 is performed in the MS part 40. Thus, results equivalent to the situation in which analysis is performed with one column, as in the past, are obtained.

When analyzing volatile organic compounds, the sample gas collected from the headspace of the liquid sample stored in the container 11 in the headspace sample introduction device 10 is introduced to the first column 22 by being swept in the carrier gas flow. At this point, in the liquid sample introduction device 14, only a prescribed quantity of carrier gas flows in the second column 23.

In the first column 22 (i.e., the column to which the sample gas was introduced), the sample components are separated, and the sample components flow into the ionization chamber 42. Mass analysis of each sample component is then performed in the MS part 40.

At this point, because no sample has been introduced into the second column 23, analysis of only the sample prepared in the headspace sample introduction device 10 is performed in the MS part 40. Thus, results equivalent to the situation in which analysis is performed with one column, as in the past, are obtained.

Figure 2A:
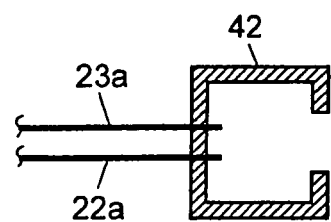
FIGS. 2(a), 2(b), and 2(c) illustrate a comparison of the configuration of column outlet ends in the GC/MS system according to one embodiment of the present invention (FIG. 2(a)), with two conventional configurations (FIGS. 2(b) and 2(c)).

As described above, in order to protect the column which is not on line for sampling, it is still necessary to flow carrier gas to that column. But, because the outlet side ends 22a, 23a of the two columns 22, 23 both are connected to the ionization chamber 42 inside the vacuum chamber 41 (see FIG. 2(a)), the open outlet ends of the respective columns 22, 23 are under a vacuum.

The line velocity of the carrier gas flowing through the column is dependent on the pressure difference between its inlet end and outlet end. That is, the line velocity of the carrier gas changes from the situation in which the outlet end of the column is under a vacuum, and the situation in which it is not under a vacuum, even when the gas pressure on the inlet end of the column is the same.

Figure 2B:
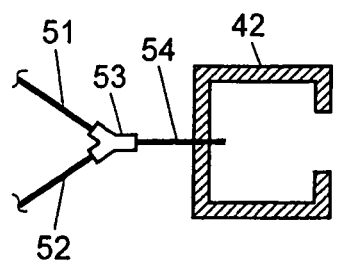

FIG. 2(b) illustrates a piping configuration on the outlet side end of a conventional column known as a double column correspondence GC/MS. The outlet ends of the two columns 51, 52 are connected by a Y- (or T-) type joint 53, and following the confluence, one sample introduction pipe 54 extends into the ionization chamber 42. In such a configuration, the gas pressure in the Y-type joint 53 is influenced by the two columns 51, 52. Thus, in this conventional configuration, the column gas line velocity, which is determined by the column inlet pressure and the column outlet pressure, is different from a situation in which there is only one column. Therefore, a shift occurs in the retention time of the sample component in the sample gas. As a result, it is necessary to perform a complex recalculation in order to determine the retention time.

Figure 2C:
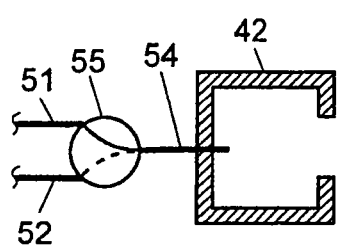

FIG. 2(c) illustrates a piping configuration in which the outlet ends of two columns 51, 52 are alternately switched with a three-way valve 55. In this case, because the path through which the carrier gas flows is completely switched by the valve 55 (e.g., when one column 51 and the sample introduction pipe 54 are connected), the outlet end is under a vacuum. Thus, the line velocity of the carrier gas should become the same as that in the case of a single column. However, when a device, such as valve 55, is inserted into the flow channel, a dead volume may result, or the peak strength may be lowered.

In the present invention, however, by virtue of the configuration, the flow rate and the line velocity of the carrier gas are the same as in the case of a single column. Furthermore, the above-described problem resulting from inserting a valve 55 also does not arise, and analysis with high precision becomes possible.

In the above description, an embodiment of the present invention was described in which agricultural chemicals are introduced by the liquid sample introduction device 14, and volatile organic compounds are introduced by the headspace sample introduction device 10. It is clear, however, that with the present invention, numerous other types of samples may similarly be analyzed.

Also, in the embodiment described above, a headspace sample introduction device and a liquid sample introduction device with a splitless system were employed as the first and second sample introduction parts. But, in another possible embodiment of the invention, one can use, for example, a combination of another sample introduction device, such as a purge/trap sample introduction device, which is suitable mainly for analysis of volatile organic compounds and mold odors in water, and a liquid sample introduction device, or a headspace sample introduction device.

Also, in still another possible embodiment of the invention, two sample introduction devices of the same type can be arranged in parallel.

Also, because the type of column used is basically selected in accordance with the type or property of the sample to be analyzed, when the two sample introduction devices are of a different type, the columns are often of a different type, but they are not necessarily limited to being different. On the other hand, when the two sample introduction devices are of the same type, because it is not very meaningful to have two columns arranged in parallel if the two columns are of the same type, the types of the two columns are typically different.

The embodiments described herein are only examples of possible embodiments of the present invention. Even if changes, additions, or corrections are made that are within the substance of the present invention, it is to be understood that such changes, additions, or corrections are covered by the scope of the claims of the present application.

The disclosure of Japanese Patent Application No. 2004-357029 filed on Dec. 9, 2004, is incorporated herein.

What is claimed is:

1. A gas chromatography/mass spectrometry system, comprising:

first and second sample introduction parts for introducing sample gases, said first sample introduction part having a carrier gas supply for introducing a carrier gas, and said second sample introduction part having a carrier gas supply for introducing a carrier gas;

a gas chromatography part comprising a first column for separating a sample component from said sample gas introduced from said first sample introduction part; a second column for separating a sample component from said sample gas introduced from said second sample introduction part; and a column oven capable of housing said first and second columns in a parallel configuration;

an interface part comprising a temperature maintenance block, through which an outlet end of each of said first and second columns is inserted; and a mass spectrometry part, comprising an ionization chamber to which said outlet ends of said first and second columns inserted through said interface part are connected; a mass separation part for mass-separating ions produced inside said ionization chamber; a detector for detecting said mass-separated ions; and a vacuum chamber for housing under a vacuum said ionization chamber, said mass separation part, and said detector, said outlet ends of said first and second columns located in the ionization chamber being under the vacuum, wherein said carrier gas supply of the first sample introduction part is arranged to supply the carrier gas for protection of the first column when said second column is operated, and said carrier gas supply of the second sample introduction part is arranged to supply the carrier gas for protection of the second column when said first column is operated.

2. The gas chromatography/mass spectrometry system according to claim 1, wherein said first and said second sample introduction parts are of a different type.

3. The gas chromatography/mass spectrometry system according to claim 1, wherein said first and said second sample introduction parts are of a same type.

4. The gas chromatography/mass spectrometry system according to claim 2, wherein said first sample introduction part is a headspace sample introduction part for collecting and delivering sample gas from a space above a liquid surface of a liquid sample stored inside a container, and said second sample introduction part is a liquid sample introduction part comprising a sample gasification chamber for gasifying an injected liquid sample.

5. The gas chromatography/mass spectrometry system according to claim 4, wherein said first column is a capillary column having polarity, and said second column is a capillary column having no polarity.

6. The gas chromatography/mass spectrometry system according to claim 1, wherein said interface part maintains a temperature of said outlet ends of said first and second columns at a same temperature as the temperature inside said column oven.

* * * * *